United States Patent [19]

Sheiman et al.

[11] Patent Number: 4,752,562

[45] Date of Patent: * Jun. 21, 1988

[54] DETECTION OF SERUM ANTIBODY AND SURFACE ANTIGEN BY RADIAL PARTITION IMMUNOASSAY

[75] Inventors: Mark I. Sheiman; Joseph L. Giegel; Mary Brotherton, all of Miami, Fla.

[73] Assignee: Baxter Travenol Laboratories, Inc., Deerfield, Ill.

[*] Notice: The portion of the term of this patent subsequent to May 14, 2002 has been disclaimed.

[21] Appl. No.: 661,939

[22] Filed: Oct. 17, 1984

Related U.S. Application Data

[63] Continuation-in-part of Ser. No. 227,664, Jan. 23, 1981, Pat. No. 4,517,288.

[51] Int. Cl.$^4$ ................. G01N 33/543; G01N 33/558
[52] U.S. Cl. ........................................... 435/5; 435/7; 435/29; 436/514; 436/515; 436/519; 436/527; 436/535; 436/541; 436/820
[58] Field of Search ................. 435/5, 7, 29; 436/514, 436/515, 527, 535, 541, 519, 820

[56] References Cited

U.S. PATENT DOCUMENTS 4,366,241 12/1982 Tom et al. ........................... 436/541
4,517,288 5/1985 Giegel et al. ....................... 436/514

Primary Examiner—Sam Rosen
Assistant Examiner—Robert Benson
Attorney, Agent, or Firm—Susan B. Fentress; R. E. Hartenberger; P. C. Flattery

[57] ABSTRACT

Disclosed is a method for detection for serum antibody and/or microbial surface antigen by radial partition immunoassay. The method of this invention is applicable to (a) the evaluation of a clinical specimen for identification of a microorganism; (b) antimicrobial sensitivity assays for determination of an efficacious antibiotic for use against a specific microorganism; (c) a semi-quantitative determination of viral surface antigen; and, (d) a quantitative method for the determination of the presence of serum antibodies to microbial antigens. In each of the foregoing applications, the analyte of interest can be immobilized within a porous matrix (solid phase) by simple pipetting of the sample onto the prepared matrix. Appropriate reagents are subsequently applied to the matrix to effect immunochemical interaction of a labeled binding material to the surface antigen (or antibody) of the analyte of interest. The portion of the matrix within which such interaction takes place is termed the "reaction zone". After a brief incubation period, a suitable wash solution is then applied to the reaction zone of the matrix so as to effect radial partitioning, entirely within the matrix, of bound and unbound labeled binding material. The amount of signal generated by the bound label remaining in the reaction zone is then monitored visually or by an appropriate measuring device.

19 Claims, No Drawings

DETECTION OF SERUM ANTIBODY AND SURFACE ANTIGEN BY RADIAL PARTITION IMMUNOASSAY

CROSS REFERENCE TO RELATED APPLICATION

This application is a continuation-in-part of copending application Ser. No. 227,664, now U.S. Pat. No. 4,517,288, filed Jan. 23, 1981 in the names of Joseph L. Giegel and Mary M. Brotherton.

BACKGROUND OF THE INVENTION

1. Field of Invention:

This invention is directed to a method and a diagnostic kit. More specifically, the invention described hereinafter relates to a method for the detection of serum antibodies to microbial antigens and/or the direct detection and quantitation of these microbial antigens by radial partition immunoassay and a test kit for the performance of such assay.

2. Description of the Prior Art:

(a) A number of the advances in the field of diagnosis of infectious disease attributable to microganisms, have been made as a direct result of automation of the microbial identification process. These advances have not only reduced the turn-around time for performance of such analysis, but have increased the accuracy of results which can be attained. The major difficulties encountered in the improvement of such assays is the need to reduce the processing interval for performance of the assay. Classically, microbe detection has involved considerable delay and expense traditionally associated with manual techniques, incubation steps, irreproducibility and unreliability of results. It has been both the hope and objective of the developers of semi- and essentially fully automated systems, that these deficiencies in the classical methods can be eliminated or minimized through the adaptation of automation to this art.

Semi-automated systems are currently commercially available for performance of the above type assay. Typically these systems employ some kind of support media (i.e., wells, cups or tubes) into which is placed an aliquot of patient sample. Added to this at different stages are signal generating reagent(s). After several sets of washings and one or more periods of incubation, a reaction of this analyte in the sample with the signal generating reagent(s) occurs. The activity of the signal generating reagent(s) is related to the amount of the analyte present in the sample. The signal measured may be a radiolabeled, a chromogenic or a fluorogenic compound which can be detected by instrumentation; or, observed visually through comparison of color change with a set of reference colors specific for the given substance being tested.

Since the rapid detection and accurate identification of the microbial species is the predominant concern of the clinical microbioloby laboratory, most of the automated systems which have been introduced are designed to reduce the amount of required manipulative steps, and also increase the efficiency of the assay process. Notwithstanding such advances, significant limitations in the state of the art still exist. Representation of one such commercially available system is MINITEK ® microorganism differentiation system (available from Becton, Dickinson and Company). This MINITEK system uses a plate containing ten (10) wells, into which are added one or more cartridge-dispensed paper discs impregnated with a substrate. A microbe colony, isolated from an incubated culture, is also added to the well. The contents of the well is then covered with a layer of mineral oil to prevent contamination. The contents are thereafter incubated for 18–24 hours. Then, as applicable, reagents are added and allowed to react with the contents of the well; the results of such interaction ultimately being determined by comparison of color changes in the liquid in the well with the appropriate reference comparator card. One of the more significant limitations of this MINITEK system as with most others which are currently being used, is the delay encountered before results can be obtained. The system requires two extended incubation periods, one to grow the microbe, and a second to allow the sample and substrate to react. The MINITEK system also is highly labor intensive, requiring several manual manipulative steps. Furthermore, the system must be used with pure cultures, it being incompatible with specimens taken directly from the patient since the presence of endogenous interactive substances in the patient sample can interfere with the accuracy of the assay. The assay results obtained from the tests performed on this system are limited in precision to a positive/negative determination or to a range of color-compared variation.

(b) Antimicrobial Sensitivity Assay techniques have been developed as a means for rapidly determining the most efficacious drug to be used in the treatment of a particular infection without the need for obtaining precise identification of the bacteria causing the infection. This method comtemplates observing which of a set of drugs best inhibits the growth in vitro of bacteria contained in a patient sample. the primary objective of this screening technique is to provide the physician with an accurate, fast and reliable basis for his choice of therapeutic agent.

Traditional anti-microbial sensitivity assay techniques are routinely accomplished by obtaining a patient sample containing the infectious agent and adding the sample to a series of test tubes containing a growth media. In all but one of the test tubes (a control), are added different antibiotics (one per tube) which are potentially useful for treatment of the individual affected with the infectious agent. Alternatively, sensitivity testing may be performed by using a petri dish containing growth media onto which the bacterium being tested is streaked. Following the placement of a series of impregnated antibiotic-containing "disc's" onto the surface of this medium, the drug of choice is determined by measuring the amount of growth after a predetermined incubation period. As with the test tube method, the region about the antibiotic showing the greatest degree of clearing (i.e., demonstrating the least amount of bacterial growth) is indicative of which drug has best inhibited the growth of the microbe. This drug is thus the drug of choice in treatment of the microbial infection. The method of measuring the degree of growth of the infectious agent in a patient sample in the presence of different drugs is the subject of this invention.

(c,d) A technique currently used for microbial antigen detection and identification is that of ELISA, or enzyme-linked immunosorbent assay. In a classical heterogeneous assay (such as described in U.S. Pat. No. 3,654,090), microbial identification is performed in a series of microtiter wells coated with antibody. This type of assay generally involves at least two incubation periods and several wash steps. Here, too, there are numerous limitations associated with the system. As with the microoganism identification systems discussed above, two incubation periods are required. Many of the other limitations and deficiencies associated with the microorganism identification systems discussed hereinabove are also present in microbial identification by an ELISA technique. Moreover, the typical microtiter plate consists of ninety-six (96) wells. If the number of assays to be performed is less than the total number of wells, the cost per test is increased proportionally.

The problems and shortcomings associated with the techniques described hereinabove are encountered to a similar extent in microbial identification assays, the determination/quantitation of viral surface antigen, and the corresponding detection of serum antibodies against these microbial antigens.

As is evident from the above discussion, there is a continuing need for improvement in the currently available techniques for surface antigen detection in the following respects: reduction in the number of manipulative steps which are performed manually by the tehnician; reduction in the time required for the performance of such assays; enhancement in the accuracy of the reliability of the test results; and, reduction in the cost per test charge to the patient.

OBJECTS OF THE INVENTION

Accordingly, it is the object of this invention is to remedy the above as well as related deficiencies in the prior art.

More specifically, it is the principal object of this invention to provide an automated method for the detection of infectious agents in fluid samples.

It is another object of this invention to provide a method for the evaluation of a patient clinical sample for identification of an infecting microorganism.

It is yet a further object of this invention to provide a method for the determination of an efficacious antibiotic by performing an anti-microbial sensitivity assay.

It is still yet a further object of this invention to provide a method for the semi-quantitative determination of viral surface antigen.

It is still yet a further object of this invention to provide a method for the identification and quantitative determination of serum antibodies to microbial antigens.

SUMMARY OF THE INVENTION

The above and related objects are achieved by providing a method for detection of microbial antigen or serum antibody to such antigen (hereafter "analyte") by radial partition immunoassay. As is appreciated, the identification of a microorganism can also be achieved indirectly through identification of characteristic products of their metabolism and/or component parts thereof resulting from the fragmentation, lysing and/or cleavage of the microorganism. The term "analyte" as used throughout this disclosure is intended as not only descriptive of infectious agents (i.e. microbes) of the type which can induce disease within a host organism and which generally proteinacious in composition or of a host-produced antibody against such an organism but also other products and/or component parts thereof which are indicative of the presence of the microorganism. The assay of a fluid sample in accordance with this method is conducted entirely within a solid, inert immobilizing porous matrix by initially applying a fluid sample containing an unknown quantity of analyte to a finite zone of the immobilizing porous matrix. The analyte is applied either as a solution or a suspension so as to permit dispersion thereof within the interstices of such matrix. The distribution of analyte within such matrix defines the boundaries of a reaction zone within this matrix. Subsequently, a labeled compound or indicator is applied as a liquid to substantially the center of the reaction zone, under conditions which allow the indicator to immunochemically bind to the analyte in an amount which can be correlated to the amount of analyte in the reaction zone. The labeled compound or indicator is usually a compound molecule consisting of a binding agent having an affinity for the analyte of interest chemically conjugated to the signal generating moiety. Following a brief incubative period, a stream of eluting solvent is applied to substantially the center of the reaction zone, the quantity of this eluting solvent being sufficient to effect a radial chromatographic separation, entirely within the immobilizing porous matrix, of unbound indicator and endogeneous materials from the indicator which is bound within the reaction zone. After such separation is effected, the extent to which the bound indicator is present within a delimited area of the reaction zone is observed by measurement with appropriate instrumentation. As a result of the foregoing separation step (radially partitioning), the delimited area of the reaction zone is essentially free of unbound indicator.

The foregoing method is applicable to an antimicrobial sensitivity assay, a microbial identification assay, the detection of microbial antigens, and the detection of antibodies to microbial and viral microbial antigens.

DESCRIPTION OF THE INVENTION INCLUDING THE PREFERRED EMBODIMENTS

The method of this invention, as applied to an antimicrobial sensitivity assay, initially involves the culturing of microbes obtained from fluid samples in vitro in a growth media containing one or more potentially effective antibiotics. The various antibiotics present in each of the cultures inhibits the growth of the microbe to a greater or lesser degree, and, thus, the test tube containing the least microbial growth is indicative of the most efficacious drug or drug combination, for the treatment of the microbial infection in the afflicted patient.

For the purposes of the description of this portion of the invention, the terms "analyte" and "microbe" are used interchangeably and contemplate microorganisms not only of bacterial size, but is also inclusive of fungi, Rickettsia, protozoa, viruses or any other mimcroorganism, which can be effectively entrapped in a prepared porous matrix of the type typically used in the filtration of bacterial cultures, i.e., Whatman Glass Microfilter Filters.

In practice, a sample of inoculum is added to each of a series of test tubes containing a growth media and, in all but one test tube, different antibiotics are added, one per test tube. The contents of each tube is thereafter suspended and subsequently incubated. An aliquot of this suspension can then be applied to a porous matrix wherein the microbe becomes entrapped and immobilized with the matix over an area which corresponds to distribution of the fluid sample therein. The distribution of the fluid within the porous matrix generally defines the boundaries of a reaction zone within which the screening method of this invention can be performed.

Since direct measurement of the concentration of microbe is difficult, the method of this invention involves the measurement of a labeled compound, whose concentration within the matrix can be correlated to the concentration to microbe of interest.

Assuming, for illustration purposes, that the immobilized microbe has characteristic surface antigens, its identification by immunochemical interaction with appropriately labeled antibody to such surface antigen(s) can be readily accomplished in accordance with radial partition immunoassay methodology, as adapted herein to the anti-microbial sensitivity assay; a comprehensive description of the technique applicable to the assays of this invention appearing in, Giegel et al, *Radial Partition Immunoassay*, Clin. Chem., 28:9, 1894 (1982); copending U.S. patent application Ser. No. 227,664, filed Jan. 23, 1981; and Spanish Patent No. 508,875 (to Giegel and Brotherton)-all of which are hereby incorporated by reference in their entirety. Following the immobilization of the microbe in the porous matrix in the manner described hereinabove, a labeled antibody is subsequently applied to the reaction zone of the porous matrix containing the sample under conditions which favor immunochemical binding of the labeled antibody with the surface antigen of the microbe entrapped in the matrix. After a brief incubation period, a stream of wash fluid is applied to the porous matrix to effect separtion of unbound materials from that portion of the reaction which is to be monitored for the presence of the microorganism of interest. In the most preferred embodiments of this invention the point of application of the aliquot of patient's sample, labeled antibody and wash fluid is essential coincident. However, so long as there is substantial overlap in the migration patterns of the fluid sample, labeled antibody and wash fluid, precise coincidence of application to the porous matrix is not required.

These unbound materials generally migrate radially from the point of application of wash fluid. Depending upon the type of label used, the level of bound labeled antibody can be monitored by measurement with the type of fluorometric or spectrophotometric devices disclosed in U.S. Pat. No. 4,059,405 (which is hereby incorporated by reference in its entirety) or by counting the amount of radioactivity in the reaction zone. The level of labeled antibody which is present in the sample is thereafter compared to a standard or control. This comparison can also be made manually (i.e., visually) or, where the monitoring of indicator level is automated, through the use of microprocessors. In the interpretation of the results of such assay, the control sample containing no antibiotic will have the highest level of labeled antibody indicating the greatest amount of growth. The samples which have been innoculated with antibodies, will have a lower level of labeled antibody, indicating inhibited growth due to the presence and relative effectiveness of the antibiotic.

As noted above, the method of this invention is performed within an inert porous matrix. The porosity of the matrix is sufficiently fine to entrap particles of microbial size thereby effectively immobilizing them within its interstices. The entrapment of the microbes within the interstices of the matrix allows for the matrix to act as a unique reaction vessel for immunochemical interactions between the analyte and the indicator. The matrix is selected so that the size of the interstitial spaces is sufficiently small to effectively immobilize microbial size particles yet allow the reaction fluid to spread, via capillary action, essentially uniformally in all directions. When an aliquot of patient sample is dispensed onto the matrix, the microbe will be principally immobilized at and peripheral to the point of application thus, defining the reaction zone for subsequent interaction with other reagents (i.e. labeled indicator). The relatively large surface area associated with a porous matrix of this nature permits the concentration of the analyte within a comparatively small area, thereby decreasing the amount of patient sample necessary to obtain satisfactory results and increasing the overall sensitivity and efficiency of the method.

This porous matrix can be composed of any material which is inert, i.e., that is will not itself react deleteriously with any materials that are brought in contact with it which are associated with the particular assay. In addition, in the context of this invention, "inertness" contemplates that the matrix will not chemically or immunologically interact with either the sample or the reagents used in performance of the assay, will not dissolve and has negligible nonspecific attraction for such materials. In those embodiments of this invention where the physical size of the analyte of interest is too small for effective physical entrapment, and therefore immobilizing the analyte within the inert matrix, the matrix can be sensitized with an appropriate agent (i.e., antibody) to bind such finer particles. As noted above, one of the principal advantges of the use of a porous matrix is its large surface area which enables concentration of the analyte of interest in a small area. In the preferred embodiments of this invention, the porous matrix is advantageously made of a mat of composed fibers, such as glass or synthetic fibers. The matrix may, however, by composed of other non-fibrous porous materials such as sintered glass, ceramics, synthetic spongy materials or polymers, etc. Since one of the essential features of the radial partition immunoassay methodology is the ability of this technique to effect rapid and complete separation of constituents of differing mobility within the matrix, the presence of anything within the matrix which would be incompatible with or inhibit the capillary flow of liquids in such matrix is obviously unsatisfactory. Thus, gelatinous solids and the like are, by definition, excluded from the category of matrices which are accpetable for use in this method. Other materials such as cellulosic paper tend to have a greater nonspecific attraction for the material applied thereto and thus may require pretreatment to inactivate their reactive sites.

The method of this invention is useful for a variety of biological assays. For example, a throat swab, blood or urine sample can be quickly and accurately analyzed for various bacterial and other microbes. Microorganism analytes of interest include: Corynebacteria, Pneumococci, Streptococci, Staphylococci and Neisseria. Some of the above mentioned microorganisms may need to be pretreated by fragmentation, lysing, cleaving, etc., in order to obtain an appropriate fraction or portion suitable for analysis. Viral assay which may be performed in accordance with the methodology of this invention includes: Adenoviruses, Herpes Viruses, Pox Viruses, Picornaviruses, Myxoviruses, Arboviruses, Reoviruses and Tumor Viruses. Hepatitis A and B as well as other forms of hepatitis can be detected by testing for the presence of hepatitis viral antigen or antibody in the patient sample. To entrap particles of smaller size within the matrix, (such as the viruses mentioned above), the matrix may have to be pretreated with an antibody or other agent. Virtually any type of biological fluid can be effectively screened in accordance with above methodology for the presence infectious agents.

As is typically done, a throat swab can be used for a bacterial screen of sputum sample to detect *Staphylococcus aureus, Haemophilus influenzae, Streptococcus pneumoniae, Psudomonas aeruginosa,* Enterobacteriaceae (group), *Neisseria meningitidis, Corynebacterium diptheriae, Streptococcus pyogenes* and *Bordetella pertussis.*

Similary, a urine screen can be utilized for detection of *Escherichia coli, Proteus mirabilis, Pseudomonas aeruginosa* or Staphylococcus Sp. Also, infectious agents which appear in blood, serum or spinal fluid can be detected using the method of this invention.

Standard dilutions of the sample in liquid medium are typically prepared so that a uniform aliquot can be added to the porous matrix.

After the analyte of interest is immobilized within the matrix, a labeled compound is introduced into the reaction zone containing the infectious agent. The purpose of the label is to provide an indirect means for measuring the amount of analyte present in the sample. The labeled compound is designed to immunochemically bind to the analyte entrapped with the matrix. A stream of eluting solvent (wash fluid) can then be applied to effect radial partitioning of unbound labeled compound and other unbound materials from that portion of the reaction zone which is to be monitored for the presence of analyte. After application of the wash fluid in the foregoing manner, only that portion of the labeled compound that has bound to the analyte which is entrapped (within the matrix) is detectable for subsequent measurement by the monitoring techniques. In an alternate embodiment of the present invention, the sample solution and solution containing the labelled compound are pre-mixed prior to application to the porous medium.

The labeled compounds suitable for use in this method can be an antibody, antigen or any other substance that selectively immunochemically binds with the analyte of interest and will either itself produce a detectable signal or interact with yet another reagent to produce a detectable signal. The synthesis of labeled compounds suitable for use in the method of this invention can be performed by well-known synthetic protocols. Typically, such synthesis involves cross-coupling, or conjugation, of an indicator molecule to an immunochemically active fragment through a bifunctional reagent. Thus, the term "conjugate" or phrase "labeled conjugate" is also used in the art throughout this disclosure interchangeable with the term "indicator" and phrase "labeled compound" respectively. Various indicators which are suitable for use in the methodology of this invention include radiolabels such as $^{125}I$ or tritium, fluorescent molecules, enzymes, cofactors, chemiluminscence reagents and compounds that become fluorscent upon subsequent enzymatic attack. In the case of radioactive indicators the concentration of the labeled compound is usually monitored by placing the porous medium having the bound labeled compound in a scintillation or gamma counter. The extent of enzyme labeled compound bound to the analyte within the reaction zone can be detected by simply contacting the bound enzyme labeled compound with a substrate, under conditions which favor enzymatic cleavage of an indicator molecule from substrate. The indicator molecule is preferably a chromogenic or fluorogenic substance that can be measured by conventional monitoring techniques. Compounds labeled with enzyme cofactors or effectors can be detected similarly by their effect on enzyme action on a substrate. Compounds labeled with chromophores may be directly measureable using fluoroscopy, ultraviolet spectroscopy or other spectroscopic or visual means.

After the labeled compound has been added to the reaction zone, in the manner described previously, a brief incubation period is generally required to permit immunochemical interaction of the labeled compound and the analyte. A clean separation of unbound label compounds, as well as interfering endogenous proteins, must then be effected from a delimited area of the reaction zone prior to the monitoring step. This separtion, or partitioning, is accomplished by applying a stream of an eluting solvent to the reaction zone in sufficient volume to effect radially chromatographic separation of unbound materials from the reaction zone. As noted previously, so long as there is substantial overlap in the patterns of distribution of the various fluids which are applied to the porous matrix, an effective separtion, or partitioning of bound and free labeled compound will occur. The solvent employed in this elution step may be water or a buffer solution in which such unbound compounds are conveniently dissolved. As the solvent migrates radially out from its point of application to the reaction zone, unbound reactants are separated from the bound reactants. A small quantity of such solvent is generally sufficient to cleanly separate the unbound reactants from at least a portion of the reaction zone. Such reactants, if visible, generally appear as one of more rings around the reaction zone, with the distance of separation only being dependent on the volume of the solvent used and the Rf values for the reactants. Small volumes of eluting solvent have been found effective for achieving good separation of free from bound reactants, thus providing a quick, economical and reliable assay procedure. Typically, solvent volumes of from about 10 microliters to about 150 microliters, and preferably 50 to 80 microliters are employed. These solvents may be conveniently applied to the reaction zone with a pipette, hypodermic syringe of other dispensing device. The volumes of fluids applied to the porous matrix in the performance of the assay for this invention are sufficient to effect an essentially homogeneous area within the reaction zone for monitoring of the analyte of interest; and, yet permit retention of all of such fluids entirely within the porous matrix containing the immobilized analyte.

Upon completion of the immunochemical reaction and the partitioning of the bound and unbound labeled compounds within the reaction zone, a delimited area of this zone is monitored, with the aid of appropriate instruments, to determine the magnitude of the signal generated by the labeled compound. The delimited area of reaction zone (generally 6–10 mm in diameter) is confined to only a portion of the matrix within which the entrapped microbes and bound labeled compound are present. This delimited area is predetermined by simple adjustment in the aperature associated with the means for detection of the level of chromophore, fluorophore or radiolabel.

The signal produced by the labeled compound, or the action of the labeled compound on a appropriate substrate, can be routinely monitored with responsive instrumentation. The type of instrumentation employed will, of course, depend upon the type of immunoassay performed and the label used. Instrumentation which is suitable for use in conjunction with the method of this invention is described in U.S. Pat. No. 4,059,405, issued Nov. 22, 1977; commonly assigned copending U.S. application of Heller, Ser. No. 401,670 filed July 26, 1982; and, in Giegel et al, "Radial Partition Immunoassay", Clinical Chemistry, 28:9, 1982; all of the above being hereby incorporated by reference in their entirely. Typically, colorimetric, ultraviolet or fluorescent assays may be used for rate determinations (kinetic assays). The rate of formation (or disappearance) of the measured chromophore or fluorophore is typically compared to a calibration standard as an indication of concentration of the analyte. Such measurements may be made directly from the surface of the porous medium, employing a front surface fluorometer or reflectometer. The method of this invention is fully compatible with automated systems and provides an accurate quantitation of the amount of analyte present in the sample. Alternatively, this method may also be used as a qualitative or semiquantitative test to determine the presence, absence or approximate indication of the level of infectious agent.

The method of this invention is also applicable to the analysis of a patient clinical sample for identification of a microorganism (or antibodies against that microorganism). One common method for the quantitation of antibodies in patient sample is the sandwich assay. The procedure for performance of various sandwich assays which are described in U.S. Pat. No. 4,376,110 (David et al) are also fully compatible with the radial partition immunoassay methodology of this invention, the David et al patent being incorporated by reference in its entirety.

A sandwich assay generally involves the binding of analyte of interest from a patient sample to either an antigen or antibody here after "ligand") which has been pre-immobilized on a porous matrix. The distribution of analyte, which is bound to the immobilized ligand defines the parameters of the reaction zone within the matrix. In one of the preferred embodiments for the detection of analytes too small to be entrapped within the matrix, the amount of immobilized ligand (sensitizing agent) within the matrix is in excess to insure essentially complete binding of the analyte of interest. Sufficient incubation period is allowed to elapse to permit immunochemical interaction of the analyte with the ligand. A labeled ligand such as a labeled antibody is thereafter applied to the reaction zone of the matrix and also allowed to interact with the analyte from the patient sample. After a second brief incubation period a wash fluid is applied to the matrix to effect radial elution of substantially all unbound labeled ligand (antibody) from at least a delimited area of the reaction zone. The signal generated by the labeled ligand can then be monitored in the manner previously described. As with the anti-microbial sensitivity assay described hereinabove, any of the traditional type of indicator, e.g., fluorescent, enzyme, cofactor, radioactive, chromatogenic, etc., can be used to label the ligand. After the labeled ligand is applied to the reaction zone and allowed to react, an eluting solvent is employed to remove any unbound material from this zone. Depending upon the particular indicator compund that is used, the eluting solvent may also contain a substrate, which, upon interaction with the bound labeled ligand, releases a detectable signal that can be measured and correlated to the concentration of analyte in the reaction zone. A delimited area of the reaction zone is monitored for the presence of the indicator.

The method of this invention is also applicable to the semi-quantitative determination of viral surface antigens or antibodies, such as Hepatitis A and B and Rubella viruses via a sandwich assay or via the other similar assays herinabove described.

Another of the significant advantages of this methodology, is its compatability with automated instrumentation (i.e. STRATUS Immunoassay System) of the type which is commercially available from American Dade Company, American Hospital Supply Corporation, this system being more fully described by Giegel et at, in an article relating to radial partition immunoassay referenced hereinabove. In this automated device, the porous matrix is retained in a self-stacking tab similar in configuration to photographic transparency, and the sample, labeled indicator and wash solution added thereto by a series of automated pipettes in the appropriate sequence. The construction of the self-stacking tab, which is compatible with the STRATUS Immunoassay System, is more fully described in U.S. Pat. No. 4,440,301 to Franklin S. Intengan, (which is hereby incorporated by reference in its entirety). The measurement of the amount of labeled indicator bound in the matrix is performed by front-surface fluorescence, and the entire procedure is microprocessor controlled. This system has the capability to perform thirty-two of the more common immunoassays which are presently performed in a clinical laboratory.

EXAMPLES

The Examples which follow further describe, define and illustrate a number of different embodiments of this invention. Parts and percentages appearing in such examples are by weight unless otherwise stipulated. The apparatus and techniques used in the preparation of reagents and/or performance or evaluation of the method of this invention are standard of as herein before described. All of the following assays are performed on a STRATUS automated immunoassay system utilizing the radial partition immunoassay methodology developed for this system. The instrument is modified as appropriate depending upon the choice of indicator.

I. IDENTIFICATION OF SPECIFIC MICROBES (OR MICROBIAL ANTIGENS)

Example 1: Detection of *Haemophilus influenzae*

1. A 50 ul sample of cerebral spinal fluid (CSF) is spotted onto the surface of a Stratus reagent tab containing preimmobilized Anti-*H. influenzae* antibody. The reagent tabs to be used with this example are prepared by premixing rabbit anti-*H. influenzae* antibody with goat anti rabbit antibody followed by spotting onto the surface of Whatman GF/F glass fiber filter paper.

2. After a 5 minute incubation, the tabs is then spotted with 50 ul of alkaline phosphatase labeled mouse anti-*H. influenzae.*

3. After an additional 5 minute incubation, unbound alkaline phosphatase labeled mouse anti-*H influenzae* is washed from the central field of view by the addition of a substrate wash solution.

4. Quantitation is performed via Stratus methodology. Appropriate positive and negative controls are also assayed using different tabs in the same run.

Example 2: Detection of *Neisseria meningitidis*

1. A 50 ul sample of cerebral spinal fluid (CSF) is spotted onto the surface of a Stratus reagent tab containing preimmobilized Anti-*N. meningitidis* antibody. The reagent tab to be used in this example is prepared by premixing rabbit anti-*N. meningitidis* antibody with goat anti rabbit antibody followed by spotting onto the surface of Whatman GF/F glass fiber filter paper.
2. After a 5 minute incubation, the tabs is then spotted with 50 ul of alkaline phosphatase labeled mouse anti-*N. meningitidis*.
3. After an additional 5 minute incubation, unbound alkaline phosphatase labeled mouse anti-*N. meningitidis* is washed from the central field of view by the addition of a substrate wash solution.
4. Quantitation is performed via Stratus methodology. Appropriate position and negative controls ae also assayed using different tabs in the same run.

Example 3: Detection of *Staphylococcus aureus*

1. A throat swab containing the clinical sample is placed into a small volume of culture broth.
2. A 50 ul sample of the suspension is then spotted onto the surface of a Stratus reagent tab containing preimmobilized Anti-*S. aureus* antibody. The tab to be used in this Example is prepared by premixing rabbit anti-*S. aureus* antibody with goat anti rabbit antibody followed by spotting onto the surface of Whatman GF/F glass fiber filter paper.
3. After a 5 minute incubation, the tabs is then spotted with 50 ul of alkaline phosphatase labeled mouse anti-*S. aureus*.
4. After an additional 5 minute incubation, unbound alkaline phosphatase labeled mouse anti-*S. aureus* is washed from the central field of view by the addition of a substrate wash solution.
5. Quantitation is performed via Stratus methodology. Appropriate positive and negative controls are also assayed using different tabs in the same run.

Examples 4–6

The procedures of Examples 1–3 are repeated except that the clinical samples are serum.

Examples 7–9

The procedures of Examples 1–3 are repeated except that the clinical samples are urine.

Examples 10–18

The procedures of Examples 1–9 are repeated except that "blank" tabs rather than those containing preimmobilized anti-microbe antibody are used in step 1. The GF/F paper has a reported average pore size of 0.7 microns and physically entrap the analyte within the matrix.

Example 19: Detection of Hepatitus B Antigen

1. A 50 ul serum sample is spotted onto the surface of a Stratus reagent tab containing preimmobilized Anti-Hepatitus antibody. The reagent tab to be used in this example is prepared by premixing rabbit anti-Hepatitus antibody with goat anti rabbit antibody followed by spotting onto the surface of Whatman GF/F glass fiber filter paper.
2. After a 5 minute incubation, the tabs is then spotted with 50 ul of alkaline phosphatase labeled mouse anti-Hepatitus.
3. After an additional 5 minute incubation, unbound alkaline phosphatase labeled mouse anti-Hepatitus is washed from the central field of view by the addition of a substrate wash solution.
4. Quantitation is performed via Stratus methodology. Appropriate positive and negative controls are also assayed using different tabs in the same run.

Example 20: Detection of Rubella Antigen

1. A 50 ul serum sample is spotted onto the surface of a Stratus tab containing preimmobilized Anti-Rubella antibody. The reagent tab to be used in this Example is prepared by premixing rabbit anti-Rubella antibody with goat anti rabbit antibody followed by spotting onto the surface of Whatman GF/F glass fiber filter paper.
2. After a 5 minute incubation, the tabs is then spotted with 50 ul of alkaline phosphatase labeled mouse anti-Rubella.
3. After an additional 5' minute incubation, unbound alkaline phosphatase labeled mouse anti-Rubella is washed from the central field of view by the addition of a substrate wash solution.
4. Quantitation is performed via Stratus methodology. Appropriate positive and negative controls are also assayed using different tabs in the same run.

Examples 21–40

The procedures of Examples 1–20 are repeated except that a fluorophore (fluorescein) is used as the label in place of the alkaline phosphatase.

Examples 41–80

The procedures of Examples 1–40 are repeated except that the assays are run in a competitive mode using alkaline phosphatase labeled antigen in place of the respective alkaline phosphatase labeled antibodies.

Examples 81–91

The procedures of Examples 1–9, 19 & 20 are repeated except that the antibody is immobilized onto the surface of the Stratus reagent tab via chemical crosslinking reagents such as glutaraldehyde.

II. IDENTIFICATION OF SPECIFIC ANTIBODIES TO MICROBES

Example 92: Detection of Serum IgM Antibodies Against Rubella.

1. A 50 ul serum sample is spotted onto the surface of a Stratus reagent tab containing preimmobilized Rubella antigen. The reagent tab to be used in this Example is prepared by premixing a complex of rabbit anti-Rubella antibody and Rubella antigen with goat anti-rabbit IgG followed by spotting onto the surface of Whatman GF/F glass fiber filter paper.
2. After a 5 minute incubation, the tabs is then spotted with 50 ul of an alkaline phosphatase labeled rabbit anti-human IgM solution.
3. After an additional 5 minute incubation, unbound alkaline phosphatase labeled rabbit anti-human IgM was washed from the central field of view by the addition of a substrate wash solution.

4. Quantitation is performed via Stratus methodology. Appropriate positive and negative controls are also assayed using different tabs in the same run.

Example 93: Identification of IgG Antibodies to Hepatitis Antigen.

1. A 50 ul serum sample is spotted onto the surface of a Stratus reagent tab containing preimmobilized Hepatitis antigen. The reagent tab to be used in this Example is prepared by premixing a complex of rabbit anti-Hepatitis and Hepatitis antigen with goat anti-rabbit IgG followed by spotting onto the surface of Whatman GF/F glass fiber filter paper.
2. After a 5 minute incubation, the tabs is then spotted with 50 ul of an alkaline phosphatase labeled rabbit anti-human IgG solution.
3. After an additional 5 minute incubation, unbound alkaline phosphatase labeled rabbit anti-human IgG is washed from the central field of view by the addition of a substrate wash solution.
4. Quatitation is performed via Stratus methodology. Appropriate positive and negative controls are also assayed using different tabs in the same run.

Example 94: Detection of IgG Antibodies to *Neisseria gonorrhoeae*

1. A 50 ul serum sample is spotted onto the surface of a Stratus reagent tab containing preimmobilized *N. gonorrhoeae* antigen. The tab to be used in this Example is prepared by premixing a complex of rabbit anti-*N. gonorrhoeae* antibody and *N. gonorrhoeae* antigen with goat anti-rabbit IgG followed by spotting onto the surface of Whatman GF/F glass fiber filter paper.
2. After a 5 minute incubation, the tabs is then spotted with 50 ul of an alkaline phosphatase labeled rabbit anti-human IgG solution.
3. After an additional 5 minute incubation, unbound alkaline phosphatase labeled rabbit anti-human IgG is washed from the central field of view by the addition of a substrate wash solution.
4. Quantitation is performed via Stratus methodology. Appropriate positive and negative controls are also assayed using different tabs in the same run.

Examples 95–97

The procedures of Examples 92–94 are repeated except that a fluorophore (fluorescein) is used as the label in place of the alkaline phosphatase.

Examples 98–103

The procedures of Examples 92–97 are repeated except that the antigen is immobilized onto the surface of the Stratus reagent tab via chemical, rather than by immunological means.

III. MICROBIAL SCREEN

Examples 104: Identification of *Staphylococcus aureus* from an "Unknown" Clinical Specimen 1. A throat swab containing the clinical sample is placed into a small volume of sterile saline.
2. A 50 ul sample of the suspension is then spotted onto the surface of a Stratus reagent tab containing preimmobilized Anti-*S. aureus* antibody. The reagent tab to be used in this Example is prepared by premixing rabbit anti-*S. aureus* antibody with goat anti rabbit antibody followed by spotting onto the surface of Whatman GF/F glass fiber filter paper.
3. After a 5 minute incubation, the tab is then spotted with 50 ul of alkaline phosphatase labeled mouse anti-*S. aureus*.
4. After an additional 5 minute incubation, unbound alkaline phosphatase labeled mouse anti-*S. aureus* is washed from the central field of view by the addition of a substrate wash solution.
5. Quantitation is performed via Stratus methodology. Appropriate positive and negative controls are also assayed using different tabs in the same run.

Examples 104–113

The procedure of Example 104 except that the microbes and rabbit antibodies against those microbes) are as follows:
a. *Haemophilus influenzae*.
b. *Streptococcus pneumoniae*.
c. *Pseudomonas aeruginosa*.
d. *Enterobacteriaceae* (group).
e. *Neisseria meningitidis*.
f. *Corynebacterium diphtheriae*.
g. *Streptococcus pyogenes*.
h. *Bordetella pertussis*.

Examples 114–123

The procedures of Examples 104–113 are repeated except that the label is a fluorophore (fluorescein) rather than alkaline phosphatase.

Examples 124–143

The procedures of Examples 104–123 are repeated except that "blank" glass fiber filter paper tabs are used (without previously immobilized antibody present).

Examples 144–163

The procedures of Examples 104–123 are repeated except that the immobilization of the antibodies within the tab is via a chemical crosslinking agent such as glutaldehyde.

IV. ANTIMICROBIAL SENSITIVITY TESTING

Example 164

1. An aliquot from a standardized inoculum obtained from a clinical sample is placed into a series of tubes containing a suitable growth medium.
2. Into each tube (with the exception of one, the "control") is placed a different antimicrobial agent that might be effective against that particular microbe.
3. The tubes are then incubated for a period of at least 1–2 hours in order to promote growth of the microorgnism.
4. An aliquot from each of the tubes is then spotted onto individual "blank" glass fiber filter paper tabs.
5. An aliquot containing a mixture of alkaline phosphatase-labeled antibodies (against the various broad groupings of microbial antigens) is then applied to the tabs.
6. The tabs are incubated for 5 minutes.
7. Addition of substrate wash solution follows the brief incubation step. Quantitation is performed via the Stratus instrument.
8. All assay valves are compared to that of the control. Decreased enzymatic activity to that of the control indicates that that antimicrobial agent is somewhat effective in inhibiting growth.

Example 165

The procedure of Example 164 is repeated except that the fluorophore fluorescein replaces the alkaline phosphatase as the label.

Example 166

The procedure of Example 164 is repeated except that the tabs contain an agent that sides in the immobilization of the microbial cells (i.e., the tabs are NOT "blank").

Examples 167–168

The procedures of Examples 164 & 166 are repeated except that the labeled antibody conjugate is omitted. The substrate in the wash solution is matched to specificity of the immobilized microorganism. The action of the microorganism on the substrate releases the fluorophore.

Examples 169–170

The procedures of Examples 164 and 166 are repeated except that the immobilized microbial cells are "lysed" by a "substrate" reagent that also contains the materials necessary to assay for a specific component released from within these microbial cells (i.e., NAD, a specific enzyme, a specific metabolite, etc.).

What is claimed is:

1. A solid phase radial partition immunoassay for detection of microbial analyte in fluid samples, said immunoassay comprising:
   (a) applying an aliquot of a fluid sample, containing an unknown level of microbial analyte, to a finite reaction zone of a solid inert porous medium so as to effectively immobilize said analyte within the reaction zone of the porous medium;
   (b) applying a labeled compound consisting essentially of an indicator conjugated to an antibody, to substantially the center of said reaction zone under conditions which favor the immunochemical interaction of the analyte with the antibody of the labeled compound within a delimited area of said reaction zone, such interaction of said labeled compound being in proportion to the amount of analyte in said delimited area;
   (c) applying a wash solution, comprising an eluting solvent, to substantially the center of the reaction zone in a quantity sufficient to effect radial chromatographic separation, within said porous medium, of the unbound labeled compound from that which is bound to the immobilized analyte within the delimited area of the reaction zone; and
   (d) observing the extent to which the bound labeled compound is present within the delimited area of said reaction zone by measurement of the level of indicator in said delimited area.

2. The assay of claim 1, wherein the porous medium consists essentially of a filter paper and said microbial analyte is physically entrapped within the interstices of said paper.

3. The assay of claim 1, wherein the porous medium is presensitized with a ligand specific for an immunochemical binding site on said microbial analyte, so as to render said medium retentive of said microbial analyte.

4. The assay of claim 1, wherein said microbial analyte is selected from a group consisting of fungi, Rickettsia, protozoa, and viruses.

5. The assay of claim 1, wherein said microbial analyte consists essentially of proteinaceous constituents of the fragmentation, lysing or cleavage of a microorganism.

6. The assay of claim 1, wherein the indicator of the labeled compound is selected from the group consisting of enzymes, fluorophores, chromophores and radioactive isotopes.

7. The assay of claim 1, wherein the indicator of the labeled compound is an enzyme and the wash solution contains a substrate for said enzyme, wherein the enzymatic action of said enzyme on said substrate results in cleavage of an indicator from said substrate.

8. The assay of claim 1, wherein said microbial analyte is Hepatitis virus.

9. The assay of claim 1, wherein said microbial analyte is Herpes virus.

10. The assay of claim 1, wherein said microbial analyte is a species of bacteria.

11. A solid phase radial partition immunoassay for detection of a microbial analyte in fluid samples, said microbial analyte consisting essentially of a soluble antigen which has been secreted by a microorganism, or a fragment of the microorganism, the immunoassay comprising the steps of:
    (a) providing a solid, inert porous medium that has been pretreated with an immobilization effective amount of an antibody which is specific for an immunochemical binding site on said microbial analyte so as to render said medium retentive of said microbial analyte;
    (b) applying an aliquot of a fluid sample, containing an unknown level of microbial analyte, to a finite reaction zone of a solid, inert medium so as to effectively immobilize said analyte within the reaction zone of the porous medium;
    (c) applying a labeled compound, consisting essentially of an indicator conjugated to an antibody, to substantially the center of said reaction zone under conditions which favor the immunochemimcal interaction of the analyte with the antibody of the labeled compound within a delimited area of said reaction zone, such interaction of said labeled compound being in proportion to the amount of analyte in said delimited area;
    (d) applying a wash solution, comprising an eluting solvent, to substantially the center of the reaction zone in a quantity sufficient to effect radial chromatographic separation, within said porous medium, of the unbound labeled compound from that which is bound to the immobilized analyte within the delimited area of the reaction zone; and
    (e) observing the extent to which the bound labeled compound is present within the delimited area of said reaction zone by measurement of the level of indicator in said delimited area.

12. The assay of claim 11, wherein the microbial analyte is a virus.

13. The assay of claim 11, wherein the sample solution and solution containing the labeled compound are pre-mixed prior to application thereof to the porous medium.

14. The assay of claim 13, wherein the microbial analyte is the hepatitis B virus, and the porous medium is pretreated with anti-serum to Hepatitis B surface antigen.

15. The assay of claim 11, wherein the microbial analyte is a viral fragment.

16. A solid-phase radial partition immunoassay for detection of serum antibody to a microbial antigen in a fluid sample, the immunoassay comprising the steps of
  (a) providing a solid inert porous medium that has been pretreated with an immobilization effective amount of antigen which is specific for an immunochemical binding site on the serum antibody so as to render said medium retentive of said antibody;
  (b) applying an aliquot of a fluid sample, containing an unknown level of said serum antibody, to a finite reaction zone of said solid inert porous medium so as to effectively immobilize said serum antibody within the reaction zone of said porous medium;
  (c) applying a labeled compound, consisting essentially of an indicator conjugated to an anti-antibody to substantially the center of said reaction zone under conditions which favor the immunochemical interaction of the antibody with the anti-antibody of the labeled compound within a delimited area of said reaction zone, such interaction of said labeled compound being in proportion to the amount of antibody in said delimited area;
  (d) applying a wash solution, comprising an eluting solvent, to substantially the center of the reaction zone in a quantity sufficient to effect radial chromatographic separation, within said porous medium, of the unbound labeled compound from the immobilized antibody within the delimited area of the reaction zone; and
  (e) observing the extent to which the bound labeled compound is present within the delimited area of said reaction zone by measurement of the level of indicator in said delimited area.

17. A solid-phase radial immunoassay for detection of a microbial analyte in fluid samples, said immunoassay comprising:
  (a) providing a solid inert porous medium that has been pretreated with an immobilization effective amount of an antibody which is specific for an immunochemical binding site on said microbial analyte so as to render said medium retentive of said microbial analyte;
  (b) applying an aliquot of a fluid sample, containing an unknown level of microbial analyte, to a finite reaction zone of said solid inert porous medium so as to effectively immobilize said analyte within the reaction zone of said porous medium;
  (c) applying a labeled compound, consisting essentially of an indicator conjugated to an antigen which is the same antigen as the microbial analyte, to substantially the center of said reaction zone of said solid inert porous medium under conditions which favor the immunochemical interaction of said antigen conjugated with an indicator with said antibody so as to effectively immobilize said antigen conjugated with an indicator within the reaction zone of the porous medium;
  (d) applying a wash solution, comprising an eluting solvent, to substantially the center of the reaction zone in a quantity sufficient to effect radial chromatographic separation, within said porous medium, of the unbound labeled compound from that which is bound to said antibody within the delimited area of the reaction zone; and
  (e) observing the extent to which the bound labeled compound is present within the delimited area of said reaction zone by measurement of the level of indicator in said delimited area.

18. The assay of claim 17, wherein said antigen conjugated with an indicator is added simultaneously with the fluid sample.

19. The assay of claim 17, wherein said antigen conjugated with an indicator is added after the fluid sample.

* * * * *